United States Patent [19]
Spits

[11] Patent Number: 4,607,630
[45] Date of Patent: Aug. 26, 1986

[54] INTRAVAGINAL CONTRACEPTIVE DEVICE
[75] Inventor: Marc Spits, Achel, Belgium
[73] Assignee: Fundatech S.A., Geneva, Switzerland
[21] Appl. No.: 617,975
[22] Filed: Jun. 6, 1984
[30] Foreign Application Priority Data Jun. 13, 1983 [NL] Netherlands ............... 8302103

[51] Int. Cl.⁴ .............................................. A61F 5/46
[52] U.S. Cl. ................................................... 128/127
[58] Field of Search ............... 128/127, 128, 129, 130, 128/132 R, 131

[56] References Cited
U.S. PATENT DOCUMENTS

| 2,061,384 | 11/1936 | Manegold | 604/330 |
| 2,321,340 | 6/1943 | Waterbury | 128/127 |
| 2,324,656 | 7/1943 | Vincent | 128/127 |
| 2,616,426 | 11/1952 | Gordon | 604/330 |
| 2,638,896 | 5/1953 | Clark | 128/127 |
| 2,664,082 | 12/1953 | Heuboski et al. | 128/127 |
| 2,676,589 | 4/1954 | Heuboski et al. | 128/127 |
| 2,704,068 | 3/1955 | Beranek | 128/127 |
| 4,261,352 | 4/1981 | Sedlacek | 128/127 |
| 4,326,510 | 4/1982 | Buckles | 128/127 |
| 4,398,532 | 8/1983 | Sweeney | 128/127 |
| 4,427,477 | 1/1984 | Milgrom | 128/127 |
| 4,450,836 | 5/1984 | Goepp et al. | 128/127 |

Primary Examiner—Robert Peshock
Assistant Examiner—Cary E. Stone
Attorney, Agent, or Firm—Kane, Dalsimer, Kane, Sullivan and Kurucz

[57] ABSTRACT

The present invention relates to an intravaginal contraceptive device such as a diaphragm or pessary. The contraceptive device of the invention comprises a central, flexible cap-like body portion engaged by the inside of a rigid inner ring with almost fixed diameter, and by an outer part lying in the plane of and around the inner ring and being connected thereto, the outer diameter of said outer part having the ability of increasing under influence of the local circumstances after being inserted into the vagina. Preferably the outer part consists of an outer ring of a material having the ability of expanding, thus increasing the diameter of the outer ring, and an elastic membrane continuously connecting the outer ring with the inner ring. The cap-like body portion, may be impregnated with a retarded release medicine such as a spermicide.

10 Claims, 4 Drawing Figures

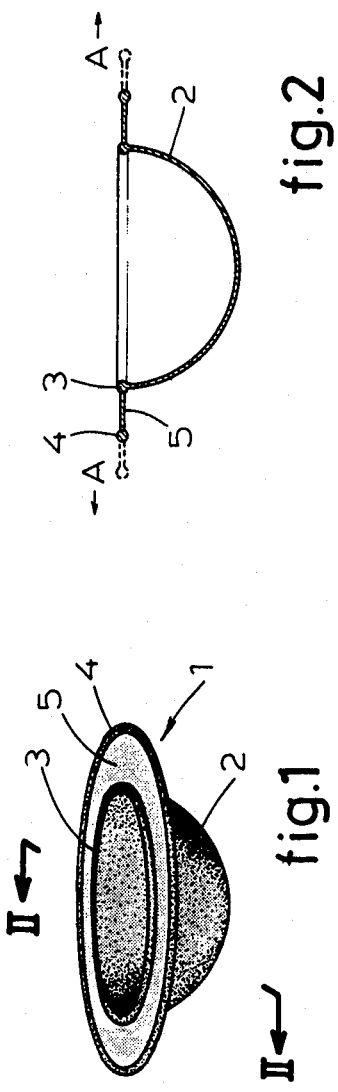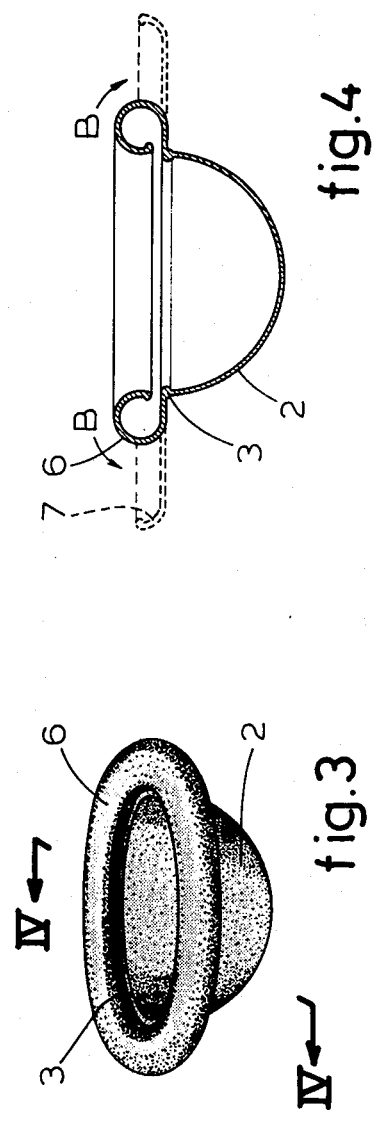

INTRAVAGINAL CONTRACEPTIVE DEVICE

BACKGROUND OF THE INVENTION

1. Field of the Invention

The present invention relates to an intravaginal contraceptive device such as a diaphragm or pessary.

2. Description of the Prior Art

Contraceptive devices of this type are already known from NL-A-78.04542. The diaphragm described in this patent application comprises a cap-like body, with a circular, somewhat rigid but nevertheless elastic peripheral structure. The edge generally comprises a spring retaining the shape of the diaphragm. Both the edge and the cap-like body may be formed of the same or different elastomers. The opposing sides of the edge may be folded together to facilitate the insertion of the diaphragm into the vagina.

After being inserted in the vaginal cavity, mostly in close proximity to the cervical os, contraceptive devices of this type form a sealing barrier between the vagina and the cervical os, the spring strongly forcing the elastic edge into engagement with the inner wall of the vagina. The sealing effect of the edge prevents spermatozoids from penetrating the uterus.

One disadvantage of the known contraceptive device of the type described above is, that their outer diameter is practically invariable, thereby limiting the applicability of said devices. As a matter of fact a diaphragm or pessary with a given diameter can only be used by a restricted group of users. As a result, the manufacturers of these devices must have an extensive assortment of diaphragms or pessaries with different diameters (e.g. ranging from 55 up to 90 mm). It will be obvious, that this leads to notable investments, while the process of manufacturing will be complicated by the diversity of the manufactured products.

The European patent application No. 79102122.3 (publication No. 6609) describes a diaphragm of the type described before, wherein the peripheral structure houses one or more adjustable shape-retaining sections, commonly made out of flexable metal. A limited possibility of adjusting the outer diameter of the contraceptive device is achieved by these adjustable shape-retaining sections. By adjusting the diaphragm, a more or less fixed shape is given to the device, but there will be no optimal adaption after inserting the device into the vaginal cavity.

Another major disadvantage, as relating to the user resides in the poor ability of the known device to adapt itself to changing conditions, to which it is subjected. The environment into which the device is placed is part of a living organism and is therefore not rigid and unchangeable. Especially the inner diameter of the vaginal cavity may change under influence of physical and mental circumstances. It is not imaginary then, that the known contraceptive device looses part of its sealing capacity, thereby reducing its reliability.

The object of the contraceptive device according to the invention is to overcome said disadvantages in an easy nevertheless effective way.

SUMMARY OF THE INVENTION

In accordance with the invention, there is provided a contraceptive device characterized by said device comprising a central, flexible cap-like body portion engaged by the inside of a rigid inner ring with almost fixed diameter, and by an outer part lying in the plane of and around the inner ring and being connected thereto, the outer diameter of said outer part having the ability of increasing under influence of the local circumstances after being inserted into the vagina. This ability of the outer diameter to be able to increase, removes the mechanical restraint, in other words, the intermolecular forces responsible for the rigidity of the material.

The circumstances causing an increase of the outer diameter of the contraceptive device after the insertion into the vaginal cavity include a difference of temperature amounting to about 20° C. between ambient temperature and the vaginal temperature, and the higher absolute humidity of the vaginal cavity compared with the ambient absolute humidity. It is also possible to remove a mechanical restraint, when the contraceptive device will be inserted by means of an insertion device.

In a preferred embodiment of the invention said outer part consists of an outer ring of a material having the ability of expanding, thus increasing the diameter of said outer ring, and an elastic membrane continuously connecting the outer ring with the inner ring.

In another preferred embodiment of the invention said outer part consists of a membrane bent along the outer circumference spirally out of the plane of the inner ring, said membrane having the ability to expand while unrolling the spiral peripheral structure and increasing the outer diameter of the outer part.

To increase the effectivity and reliability of the device further it is possible to impregnate said central cap-like body portion with a spermicide, which is retardedly released after the device has been inserted into the vagina. Besides the use of a spermicide, it is possible to impregnate the cap-like body portion with a medecine, such as antibiotics, fungicides, desinfectants and/or steroids. In this case the contraceptive device will be inserted into the vaginal cavity for a longer period, and is preferably open.

BRIEF DESCRIPTION OF DRAWINGS

FIG. 1 is a first embodiment of the contraceptive device according to the invention, comprising an elastic membrane connecting the inner and the outer ring;

FIG. 2 is a sectional view of the device of FIG. 1 as taken along line II—II;

FIG. 3 is a second embodiment of the contraceptive device according to the invention, comprising a spiral membrane; and FIG. 4 is a sectional view of the device of FIG. 3 as taken along line IV—IV.

DESCRIPTION OF THE PREFERRED EMBODIMENTS

Referring in detail to the drawings, there is shown in FIG. 1 an intravaginal contraceptive device 1, comprising a cap-like body portion 2, a rigid inner ring 3 and an outer ring 4 being connected therewith by an elastic membrane 5. The central cap-like body portion 2 functions as a collecting means for the sperm that is inserted into the vagina during intercourse, and is made out of an impenetrable flexible material. The cap-like body portion 2 is secured to the inner ring 3, which is sufficiently firm for substantially retaining its shape, also under varying circumstances. The inner ring 3 may be made of the same material as the cap-like body portion and may be stiffened by any local heat-treatment, or by a metal embedded in plastic.

The outer ring 4 consists of a material having the property to expand strongly under the influence of a raise of temperature or an absorption of fluid. The diameter of the pessary 1, which is defined by the diameter of the outer ring 4 increases almost proportional to the expansion of the outer ring 4. The outer ring 4 will expand until the forces exerted upon the ring by the vaginal wall will not allow any further expansion. Furthermore the elastic membrane 5 will exert a force upon the ring 4, said force being directed to the centre of the device.

FIG. 2 shows the principle of the embodiment of FIG. 1 of a contraceptive device according to the invention. The bold-faced position represents the device 1 before insertion into the vaginal cavity. The dotted position represents one possible position after the insertion. The arrows A show the direction into which the outer ring 4 is replaced. Meanwhile the inner ring 3 and the cap-like body portion 2 remain virtually unchanged.

The contraceptive device of FIG. 3 comprises the cap-like body portion 2, the rigid inner ring 3 and an outer part with a spirally bent peripheral structure 6. The cap-like body portion 2 and the inner ring 3 are identical to those represented in FIG. 1. The spiral, peripheral structure 6 consists of a material which can strongly expand under the influence of a raise of temperature or an absorption of fluid. In its starting position (low temperature and/or low moist content) the peripheral structure 6 has a premoulded spiral structure. When the material of the peripheral structure 6 expands, the peripheral structure is unrolled, as shown in FIG. 4, arrow B. The outside diameter of the device, as defined by the peripheral structure strongly increases, until the device will be in an equilibrium state, as described before, wherein the internal and external forces will compensate each other.

The upstanding ends 7 of the spiral peripheral structure 6 form an effective and reliable barrier in the vagina. In the embodiment of FIG. 1 the outer ring 4 may have an elliptical cross-section, with its major axis perpendicular to the plane of the ring. As a result the surface of contact between the pessary 1 and the vaginal wall is enlarged, increasing the sealing effect of the pessary. Eventually, to increase the reliability of the contraceptive device even more, it is possible to impregnate the cap-like body portion 2 with a spermicide, which is slowly released after the device has been inserted. It is noted, that the material of the outer ring may also consist of two or more metals having different coefficients of expansion.

The invention is not limited to the embodiments described above, but may be varied in many ways within the scope of the present invention.

What is claimed is:

1. Intravaginal contraceptive device such as a diaphragm or pessary, characterized by said device comprising a central, flexible cap-like body portion engaged by the inside of a rigid inner ring with almost fixed diameter, and by an outer part lying in the plane of and around the inner ring and being connected thereto, said outer part consisting of a membrane bent along the outer circumference spirally out of the plane of the inner ring, said membrane being made of a material having the ability of expanding under the influence of the local circumstances after being inserted into the vagina, thus unrolling the spiral peripheral structure and increasing the outer diameter of the outer part.

2. Contraceptive device according to claim 1, characterized in that said material to be expanded in the vagina is a material which expands under the influence of a raise of temperature.

3. Contraceptive devices according to claim 1, characterized in that said material to be expanded in the vagina is a material which expands under the influence of an absorption of fluid.

4. Contraceptive device according to claim 1, characterized by said outer diameter of the outer part being increased after being inserted into the vagina, said ability to increase, thereby removing the mechanical restraint.

5. Contraceptive device according to claim 1, characterized in that said cap-like body portion is impregnated with a spermicide and/or a medicine, which are slowly released after the device has been inserted into the vagina.

6. Intravaginal contraceptive device such as a diaphragm or pessary, characterized by said device comprising a central, flexible cap-like body portion engaged by the inside of a rigid inner ring with almost fixed diameter, and by an outer part lying in the plane of and around the inner ring and being connected thereto, said outer part consisting of a membrane bent along the outer circumference spirally out of the plane of the inner ring, said membrane being made of a material having the ability of expanding under the influence of the local circumstances after being inserted into the vagina, thus unrolling the spiral peripheral structure and increasing the outer diameter of the outer part.

7. Contraceptive device according to claim 6, characterized in that said material to be expanded in the vagina is a material which expands under the influence of a raise of temperature.

8. Contraceptive device according to claim 6, characterized in that said material to be expanded in the vagina is a material which expands under the influence of an absorption of fluid.

9. Contraceptive device accordingly to claim 6, characterized by said outer diameter of the outer part to increase after being inserted into the vagina, thereby removing the mechainical restraint, which prevented the increase of the outer diameter of the outer part.

10. Contraceptive device according to claim 6, characterized in that said cap-like body portion is impregnated with a spermicide and/or a medicine, which are slowly released after the device has been inserted into the vagina.

* * * * *